(12) United States Patent
Fischell et al.

(10) Patent No.: US 7,252,679 B2
(45) Date of Patent: Aug. 7, 2007

(54) STENT WITH ANGULATED STRUTS

(75) Inventors: David R. Fischell, Fair Haven, NJ (US); Robert E. Fischell, Dayton, MD (US); Tim A. Fischell, Richland, MI (US)

(73) Assignee: Cordis Corporation, Miami Lakes, FL (US)

( * ) Notice: Subject to any disclaimer, the term of this patent is extended or adjusted under 35 U.S.C. 154(b) by 350 days.

(21) Appl. No.: 09/950,956

(22) Filed: Sep. 13, 2001

(65) Prior Publication Data
US 2003/0050688 A1    Mar. 13, 2003

(51) Int. Cl.
A61F 2/06    (2006.01)
(52) U.S. Cl. .................................... 623/1.11
(58) Field of Classification Search ............. 623/1.34, 623/1.15, 1.3, 1.31, 1.37; 606/191, 192, 606/194, 195, 198, 108
See application file for complete search history.

(56) References Cited

U.S. PATENT DOCUMENTS

| | | |
|---|---|---|
| 3,657,744 A | 4/1972 | Ersek |
| 4,441,216 A | 4/1984 | Ionescu et al. |
| 4,503,569 A | 3/1985 | Dotter |
| 4,553,545 A | 11/1985 | Maass et al. |
| 4,580,568 A | 4/1986 | Gianturco |
| 4,733,665 A | 3/1988 | Palmaz |
| 4,776,337 A | 10/1988 | Palmaz |
| 4,800,882 A | 1/1989 | Gianturco |
| 4,856,516 A | 8/1989 | Hillstead |
| 4,886,062 A | 12/1989 | Wiktor |

(Continued)

FOREIGN PATENT DOCUMENTS

DE    32 05 942 A1    9/1983

(Continued)

OTHER PUBLICATIONS

European Search Report, dated Dec. 2, 2003, for European Pat. No. EP 02 25 6355.

*Primary Examiner*—Eduardo C. Robert
*Assistant Examiner*—Michael J. Araj (57) ABSTRACT

The present invention uses sets of strut members where the most distal set of strut members is similar to that of most stents in that the plane of the distal set of strut members is perpendicular to the stent's longitudinal axis. The present invention has a multiplicity of circumferential sets of strut members, but only the distal set of strut members has its plane perpendicular to the stent's longitudinal axis. The more proximal sets of strut members are angulated, so that the plane of the most proximal set of strut members has a preset angle such as 30°, 45° or 60° relative to the stent's longitudinal axis. The stent could also be formed from or coated with a highly radiopaque material. Alternately, a radiopaque marker could be placed at the most proximal point of the angulated, side branch stent, for the stent has to be rotated by the clinician until the plane of the most proximal angulated set of strut members is situated to be approximately parallel to the plane of the ostium of the side branch. It is also envisioned to widen the diagonal sections of the most proximal circumferential set of strut members to increase their radiopacity as compared to the radiopacity of the more distal circumferential sets of strut members. This can assist the clinician who places the side branch stent to have it properly placed at the ostium of the side branch.

13 Claims, 5 Drawing Sheets

U.S. PATENT DOCUMENTS

| | | |
|---|---|---|
| 4,907,336 A | 3/1990 | Gianturco |
| 4,969,458 A | 11/1990 | Wiktor |
| 4,990,131 A | 2/1991 | Dardik et al. |
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco et al. |
| 5,041,126 A | 8/1991 | Gianturco |
| 5,064,435 A | 11/1991 | Porter |
| 5,102,417 A | 4/1992 | Palmaz |
| 5,104,404 A | 4/1992 | Wolff |
| 5,116,365 A | 5/1992 | Hillstead |
| 5,122,154 A | 6/1992 | Rhodes |
| 5,131,908 A | 7/1992 | Dardik et al. |
| 5,133,732 A | 7/1992 | Wiktor |
| 5,135,536 A | 8/1992 | Hillstead |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,307 A | 3/1993 | Wall |
| 5,195,984 A | 3/1993 | Schatz |
| 5,217,483 A | 6/1993 | Tower |
| 5,222,971 A | 6/1993 | Willard et al. |
| 5,246,445 A | 9/1993 | Yachia et al. |
| 5,258,021 A | 11/1993 | Duran |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,334,301 A | 8/1994 | Heinke et al. |
| 5,342,387 A | 8/1994 | Summers |
| 5,354,257 A | 10/1994 | Roubin et al. |
| 5,354,308 A | 10/1994 | Simon et al. |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,382,261 A | 1/1995 | Palmaz |
| 5,387,235 A | 2/1995 | Chuter |
| 5,389,106 A | 2/1995 | Tower |
| 5,395,390 A | 3/1995 | Simon et al. |
| 5,397,355 A | 3/1995 | Marin et al. |
| 5,403,341 A | 4/1995 | Solar |
| 5,405,377 A | 4/1995 | Cragg |
| 5,411,549 A | 5/1995 | Peters |
| 5,421,955 A | 6/1995 | Lau et al. |
| 5,423,885 A | 6/1995 | Williams |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,496,365 A | 3/1996 | Sgro |
| 5,527,354 A | 6/1996 | Fontaine et al. |
| 5,569,295 A | 10/1996 | Lam |
| 5,591,197 A | 1/1997 | Orth et al. |
| 5,632,763 A | 5/1997 | Glastra |
| 5,643,312 A | 7/1997 | Fischell et al. |
| 5,649,952 A | 7/1997 | Lam |
| 5,653,747 A | 8/1997 | Dereume |
| 5,669,924 A | 9/1997 | Shaknovich |
| 5,690,642 A * | 11/1997 | Osborne et al. ............ 623/1.11 |
| 5,695,516 A * | 12/1997 | Fischell et al. ............. 606/194 |
| 5,697,971 A | 12/1997 | Fischell et al. |
| 5,755,734 A | 5/1998 | Richter et al. |
| 5,800,508 A | 9/1998 | Goicoechea et al. |
| 5,861,027 A | 1/1999 | Trapp |
| 5,876,449 A | 3/1999 | Starck et al. |
| 5,893,887 A | 4/1999 | Jayaraman |
| 5,911,754 A | 6/1999 | Kanesaka et al. |
| 5,948,016 A * | 9/1999 | Jang ......................... 623/1.11 |
| 6,165,195 A * | 12/2000 | Wilson et al. .............. 606/194 |
| 6,183,506 B1 | 2/2001 | Penn et al. |
| 6,190,403 B1 | 2/2001 | Fischell et al. |
| 6,210,431 B1 | 4/2001 | Power |
| 6,231,598 B1 * | 5/2001 | Berry et al. ................ 623/1.15 |
| 6,264,686 B1 * | 7/2001 | Rieu et al. .................. 623/1.16 |
| 6,273,910 B1 | 8/2001 | Limon |
| 2001/0016767 A1 | 8/2001 | Mauch et al. |

FOREIGN PATENT DOCUMENTS

| | | |
|---|---|---|
| EP | 0 504 290 A2 | 5/1993 |
| EP | 0 540 290 A3 | 5/1993 |
| EP | 0 679 372 A | 11/1995 |
| EP | 0 800 801 A1 | 10/1997 |
| EP | 0 830 853 A1 | 3/1998 |
| EP | 0 734 698 B1 | 8/1998 |
| EP | 0 891 751 A | 1/1999 |
| EP | 0 916 317 A | 5/1999 |
| EP | 1 042 997 A | 10/2001 |
| FR | 566 807 | 2/1924 |
| GB | 1 205 743 A5 | 9/1970 |
| WO | WO 96/26689 A1 | 9/1996 |
| WO | WO 96/34580 A1 | 11/1996 |
| WO | WO 97/25000 A1 | 7/1997 |
| WO | WO 98/19628 A1 | 5/1998 |

* cited by examiner

STENT WITH ANGULATED STRUTS

FIELD OF USE

This invention is in the field of stents, that are used to maintain patency of a vessel of the human body.

BACKGROUND OF THE INVENTION

It has been shown that intravascular stents are an excellent means to maintain the patency of blood vessels following balloon angioplasty. As stent technology has advanced, more and more complex anatomy has been treatable with stents. A particularly difficult anatomy to treat is that of a bifurcation in a blood vessel at the ostium of a side branch.

Fischell et al., U.S. Pat. No. 5,749,825, describes a stent system for bifurcations. The Fischell design has two guide wire lumens allowing the deployment of a stent in the first blood vessel while leaving a guide wire positioned through the stent struts into the second vessel which is a side branch.

The Fischell design needed several modifications for universal use. First, by needing two guidewires, the profile (outside diameter) of the stenting system is significantly larger as compared to a stent delivery catheter that uses a single guide wire. Second, the Fischell design does not address placing a stent into the second branch across the ostium, which is often not at a 90-degree angle to the first vessel.

A bifurcation stent delivery catheter with two distal balloons and one stent segment for each of the two vessels would give the capability of stenting the second branch vessel, but such a device would be larger in profile and harder to deliver than the Fischell device. If one places a first stent into a main artery with that stent being positioned across the ostium of the side branch, and the side branch is not at a 90-degree angle to the main branch, then either the second stent will extend into the main branch of the artery or some portion of the arterial wall at the ostium will not be properly supported by the second stent.

Most current tubular stents use a multiplicity of circumferential sets of strut members connected by either straight longitudinal connecting links or undulating longitudinal flexible links. The circumferential sets of strut members typically are formed from a series of diagonal sections connected to curved sections, so as to form a circumferential, closed-ring, zig-zag structure. This structure opens up as the stent expands to form the elements of the stent that provide structural support for the arterial wall. A "single strut" member is defined for use herein as a diagonal section connected to a curved section within one of the circumferential sets of strut members.

The terms "side branch" and "bifurcation" will be used interchangeably throughout this specification.

SUMMARY OF THE INVENTION

It is highly desirable after placing a first stent into the "main branch" of an artery and inserting a guide wire through the side of the expanded stent and into a side branch, to be able to place a stent across the ostium of the angled side branch (or bifurcation) where the second stent provides support to scaffold the arterial wall at the ostium of the side branch without having the stent extend into the main branch. The present invention uses sets of strut members where the most distal set of strut members is similar to that of most stents in that the plane of the distal set of strut members is perpendicular to the stent's longitudinal axis. The present invention has a multiplicity of circumferential sets of strut members, but only the distal set of strut members has its plane perpendicular to the stent's longitudinal axis. The more proximal sets of strut members are angulated, so that the plane of the most proximal set of strut members has a preset angle such as 30°, 45° or 60° relative to the stent's longitudinal axis. The stent could also be formed from or coated with a highly radiopaque material. Alternately, a radiopaque marker could be placed at the most proximal point of the angulated, side branch stent, for the stent has to be rotated by the clinician until the plane of the most proximal angulated set of strut members is situated to be approximately parallel to the plane of the ostium of the side branch. It is also envisioned to widen the diagonal sections of the most proximal circumferential set of strut members to increase their radiopacity as compared to the radiopacity of the more distal circumferential sets of strut members. This can assist the clinician who places the side branch stent to have it properly placed at the ostium of the side branch.

The clinician first determines the angle that the side branch makes with the main artery to which it is connected. The clinician then selects an angulated side branch stent that most closely matches that angle. For example, if the side branch makes an angle of 40 degrees with the main artery, the clinician might select a side branch stent having an angle of 45degrees between the plane of the most proximal set of strut members and the stent's longitudinal axis. Then, after placing a first stent into a main artery, the clinician would place a guide wire through the side of the expanded stent in the artery's main branch and advance the guide wire into the side branch. If necessary, the clinician might use a balloon of a balloon angioplasty catheter to open the struts of the first stent to "un-jail" the ostium of the side branch. The present invention stent would then be inserted over a guide wire that has been advanced through the struts of the first stent and into the side branch. The present invention stent would then be rotated until the plane of the most proximal angulated set of strut members is parallel to the plane of the ostium of the side branch. The present invention stent would then inflated across the ostium of the side branch providing good scaffolding because of the angulated struts which are the most proximal set of strut members of the side branch stent.

A key to rotatability of the present invention is in the design of the stent delivery catheter. The stent delivery catheter must be highly torqueable by the clinician, i.e., there must be a close to one-to-one correlation between how the clinician rotates the proximal end of the stent delivery catheter and how the distal portion including the stent rotates. The present invention envisions modifications of both over-the-wire and rapid exchange stent delivery catheters to provide enhanced torqueability for proper rotation and alignment of the angulated stent into a side branch.

Fischell et al., U.S. patent application Ser. No. 09/444,104 entitled "Stent Delivery Catheter With a Fixed Guide Wire", describes a stent delivery catheter with a fixed guide wire. This stent delivery catheter is designed to be highly torqueable to allow for proper steering of the fixed guide wire. It is certainly envisioned that the system described in the fixed wire stent patent application can be used for the side branch stent as described herein.

Fischell et al., in U.S. Pat. No. 5,830,227 incorporated herein by reference, describes a balloon angioplasty catheter with a rapid exchange tip. This device, when combined with the more proximal portions of the stent delivery catheter with fixed wires could be both low profile and provide for good delivery of a side branch stent. It is also envisioned that a standard over-the-wire balloon angioplasty catheter with enhanced torqueability can be produced that would also serve to rotate into position and properly deliver the side branch stent that is described herein.

The present invention stent may have one or more standard circumferential sets of strut members at the distal end of the stent and an angulated set of strut members at the proximal end of the stent. To keep the stent cell size small it may be desirable to have the most proximal set of strut members be the most angulated, with each successive set of strut members as taken in the distal direction becoming less angulated, until the plane of the most distal set of strut members is perpendicular to the stent's longitudinal axis.

The present invention stent delivery catheter may include a non-compliant balloon mounted on a catheter shaft with enhanced torqueability. It is also clear that if the main branch of an artery is essentially free of plaque build-up and only a side branch with an angled ostium is stenosed, then the present invention stent would be ideally suited for elective stenting of the side branch without prior stenting of the main branch. An example of such a use is for stenting at the ostium of a renal artery where it joins the aorta.

Thus it is an object of this invention to have a stent with its most proximal set of strut members being generally in a plane that is angulated and not perpendicular to the stent's longitudinal axis.

Another object of this invention is to have more than one angulated set of strut members near the proximal end of the stent Still another object of this invention is to have the most distal set of strut members be a standard "open slot" set of strut members with the plane of the distal set of strut members being perpendicular to the stent's longitudinal axis.

Still another object of this invention is to have the plane of the angulated sets of strut members change in angle with respect to the stent's longitudinal axis with the most angulated set of strut members being at the proximal end of the stent.

Still another object of this invention is to have at least one radiopaque marker to indicate the position of the most proximal strut of the angulated stent in order to provide the clinician with a clear indication of the correct rotational alignment of the stent at the ostium of a side branch.

Still another object of this invention is to have enhanced radiopacity for the most proximal angulated circumferential set of strut members to assist the clinician in rotating the side branch stent to make the plane of the most proximal set of strut members to be situated approximately parallel to the plane of the ostium of the side branch.

Still another object of this invention is to have a method for stenting at the ostium of a side branch comprising: first stenting the main branch, then placing a guide wire through the first stent's struts into the side branch; dilating with a balloon catheter to unjail the ostium of the side branch; inserting the present invention stent mounted on a balloon into the side branch; rotating the side branch stent until the plane of the most proximal set of strut members is approximately parallel to the plane of the ostium of the side branch and then deploying the side branch stent.

Still another object of the present invention is to have a stent delivery catheter for side branch stenting having a catheter shaft with enhanced torqueability.

Still another object of the present invention is to have a fixed wire stent delivery catheter that includes a side branch stent.

Still another object of the present invention is to have a self-expanding stent having its most proximal set of strut members having a plane that is angulated relative to the stent's longitudinal axis thereby being adapted for deployment at the ostium of a side branch.

These and other objects and advantages of this invention will become obvious to a person of ordinary skill in this art upon reading of the detailed description of this invention including the associated drawings.

DETAILED DESCRIPTION OF THE DRAWINGS

Figure 1A:
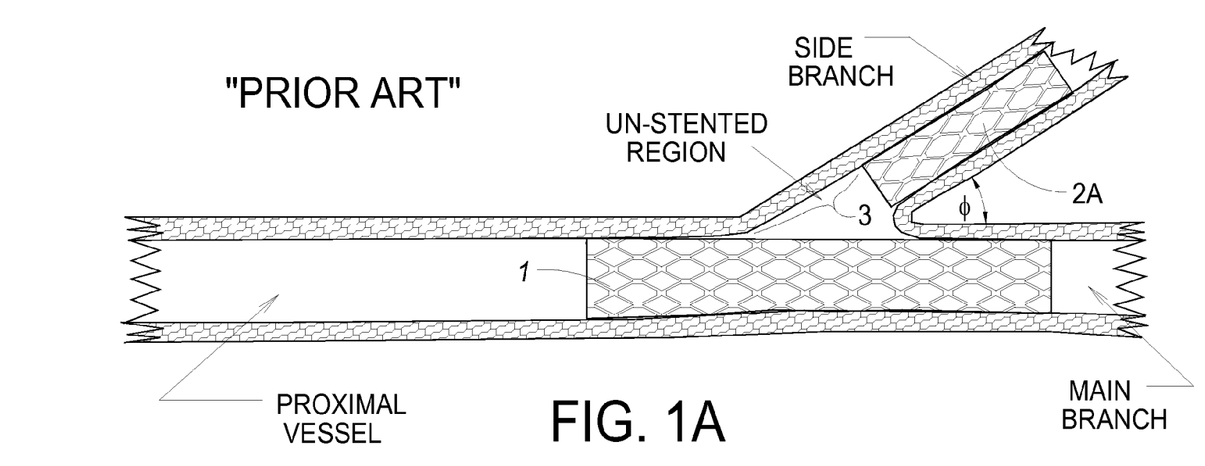
FIG. 1A is cross section of the prior art showing an artery with a side branch where a first stent is placed into the main branch and a second stent is placed into a side branch leaving part of the wall of the side branch unsupported.

FIG. 1A shows an artery with a side branch, (i.e., a bifurcated artery) where a first "prior art" stent 1 has been deployed into the main branch and a second "prior art" stent 2A has been deployed into the side branch leaving the section 3 of the arterial wall at the ostium of the side branch un-stented and therefore unsupported. The side branch vessel attaches to the main branch at an acute angle=that is less than 90 degrees. An angle==90 degrees would be a perpendicular attachment.

Figure 1B:
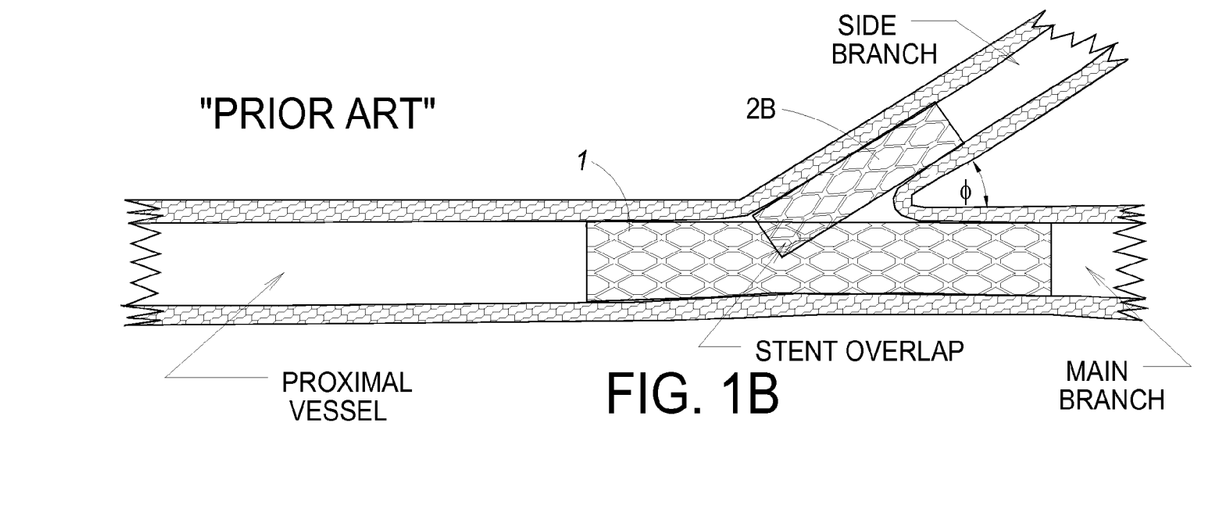
FIG. 1B is a cross section of the prior art showing an artery with a side branch where a first stent is placed in the main branch and a second stent is placed into a side branch where a proximal portion of the second stent extends part way into the main branch.

FIG. 1B shows an artery with side branch where a first "prior art" stent 1 has been deployed into the main branch and a second "prior art" stent 2B has been deployed into the side branch. In FIG. 1B, the second stent 2B extends part way into the main branch causing the stents to overlap. Such an extension of metal into an artery can cause turbulent blood flow that can readily result in subacute thrombosis.

Figure 2A:
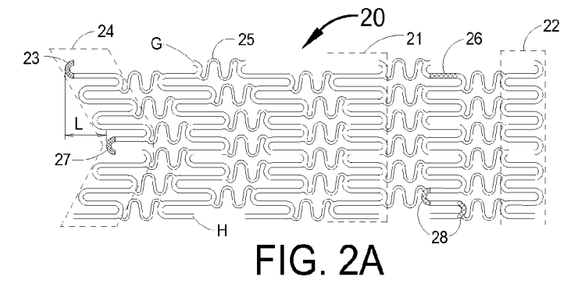
FIG. 2A is a layout view of one embodiment of the present invention stent.

FIG. 2A is a flat layout view of one embodiment of a cylindrical side branch stent 20. The stent 20 has "N" shaped flexible connecting links 25. The stent 20 is shown in its crimped pre-deployed state as it would appear if it were cut longitudinally and then laid out into a flat, 2-dimensional configuration. It should be clearly understood that the stent 20 is in fact cylindrical in shape, which cylindrical shape would be obtained by rolling the flat configuration of FIG. 2A into a cylinder with the top points "G" joined to the bottom points "H".

The stent 20 comprises a multiplicity of centrally located, longitudinally separated, circumferential sets of strut members 21 and distal end and proximal end sets of strut members 22 and 24 respectively. Each set of strut members 21, 22, or 24 is a cylindrical, closed, zig-zag, ring-like section of the stent 20 consisting of a multiplicity of curved sections 28 connected to diagonal sections 26. Except at the distal and proximal ends of the stent 20, every curved section 28 is attached to a flexible "N" link 25. Such an attachment makes the stent 20 classified as a "closed cell" or "fully-connected" stent. The unique feature of the stent 20 that makes it well suited for placement into the ostium of a side branch vessel is the angulation of the most proximal set of strut members 24. Unlike the set of strut members 22 at the distal end of the stent 20, the set of strut members 24 is angulated with a longitudinal distance "L" between the outside of the most proximal curved section 23 of the set of strut members 24 and the outside of the most distal curved section 27 of the proximal set of strut members 24. As the set of strut members 24 is cylindrical in nature, this allows for alignment of the set of strut members 24 with the angulated ostium of a side branch vessel. If "L" is relatively small, then the side branch stent 20 will be well suited for vessels with an angle=at nearly 90 degrees to the main branch. As "L" increases, the stent 20 becomes well suited for side branch vessels that are at angles=less than 90 degrees. One can envision a set of side branch stent products having three key dimensions, length, diameter and angle. For 90 degrees a prior art stent will suffice, for nearly zero degrees (a bifurcation that is essentially parallel to the main branch), three prior art stents can be used with one placed in the main branch before the bifurcation and one in each leg of a bifurcation. The present invention is most applicable to angles between 10 and 80 degrees and might be produced with angles of 15, 30, 45, 60 and 75 degrees to meet the needs of most bifurcated arteries of a human body.

The stent 20 is typically fabricated by laser machining of a cylindrical. thin-walled, metal tube. The stent 20 would be formed from or coated with a highly radiopaque material so that the angulated set of strut members 24 can be visualized for alignment with the ostium of the side branch before deployment of the stent. If the entire stent 20 is not formed from a radiopaque metal, then at least the most proximal set of strut members 24 should be made from a highly radiopaque metal. For example, a stent with a gold coating to produce a more radiopaque end set of strut members as described by Fischell et al., in U.S. Pat. No. 6,086,604, could be used for the side branch stent.

Figure 2B:
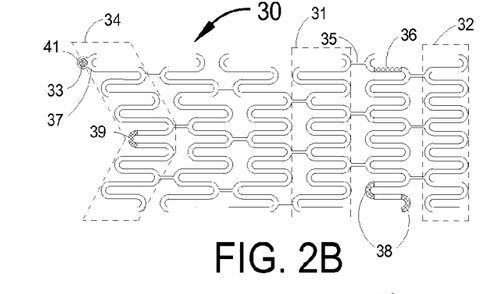
FIG. 2B is a layout view of a second embodiment of the present invention stent.

FIG. 2B is a flat layout view of a second embodiment of the present invention stent 30. The stent 30 has straight links 35 connecting the sets of strut members, but not on every curved section 38. The stent 30 comprises a multiplicity of centrally located, longitudinally separated, sets of strut members 31 and distal end and proximal end sets of strut members 32 and 34 respectively. The sets of strut members 31, 32 and 34 are connected to each other by longitudinally extending straight links 35. Each set of strut members 31, 32, or 34 is a cylindrical, closed, zig-zag, ring-like section of the stent 30 consisting of a multiplicity of curved sections 38 connected to diagonal sections 36. In the center of the stent 30, not all of the curved sections 38 are attached to a straight connecting links 35. Such an attachment makes the stent 30 classified as an "open cell" stent or a stent that is not "fully connected". The unique feature of the stent 30 making it well suited for placement into the ostium of a side branch is the shape of the most proximal set of strut members 34. Unlike the set of strut members 32 at the distal end of the stent 30, the set of strut members 34 is angulated like the set of strut members 24 of the stent 20 of FIG. 2A. As the set of strut members 34 is cylindrical in nature, this allows for alignment of the proximal set of strut members 34 with the angulated ostium of a side branch vessel.

Figure 2C:
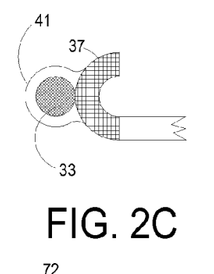
FIG. 2C is an enlargement of the radiopaque marker of FIG. 2B

FIGS. 2B and 2C illustrate a radiopaque marker 33 placed into a marker holder 41 attached to the most proximal curved section 37 of the proximal set of strut members 34. The radiopaque marker 33 allows for better visualization of the most proximal side of the angulated set of strut members 34 and also provides the implanting clinician with an indication of the correct rotational position for the stent 30 at the ostium of the side branch. This feature also allows the stent 30 to be made from a less radiopaque material such as Nitinol or stainless steel.

It is also envisioned that more than one such marker could be attached to the most proximal set of strut members 34. Ideally, one marker would be attached to the most proximal of the curved sections 37 of the end set of strut members 34 and a second marker would be attached to the least proximal of the proximal curved sections 39. The use of two such markers would assist the implanting clinician in accurately placing the side branch stent into the ostium of a side branch.

Figure 2D:
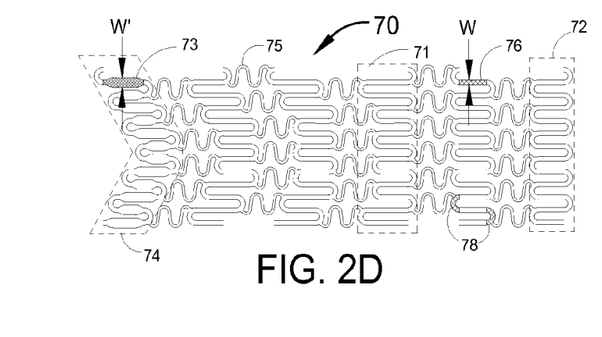
FIG. 2D is a layout view of a third embodiment of the present invention stent.

FIG. 2D is a flat layout view of a third embodiment of the present invention stent 70. The stent 70 comprises a multiplicity of centrally located, longitudinally separated, sets of strut members 71 and distal end and proximal end sets of strut members 72 and 74 respectively. Each set of strut members 71, 72, or 74 is a cylindrical, closed, zig-zag, ring-like section of the stent 70 consisting of a multiplicity of curved sections 78 connected to diagonal sections 76. Except at the distal and proximal ends of the stent 20, every curved section 28 is attached to a flexible "N" link 75. Such an attachment makes the stent 70 classified as a "closed cell" or "fully connected" stent. The stent 70 is very similar to the stent 20 of FIG. 2A with the difference being in the greater width "W'" of the diagonal sections 73 of the most proximal set of strut members 74 as compared to the width "W" of the other diagonal sections 76. This increased width of the diagonal sections 73 will make the most proximal angulated set of strut members 74 more visible and improve the ability to align it properly with the plane of the ostium of a side branch.

Figure 3A:
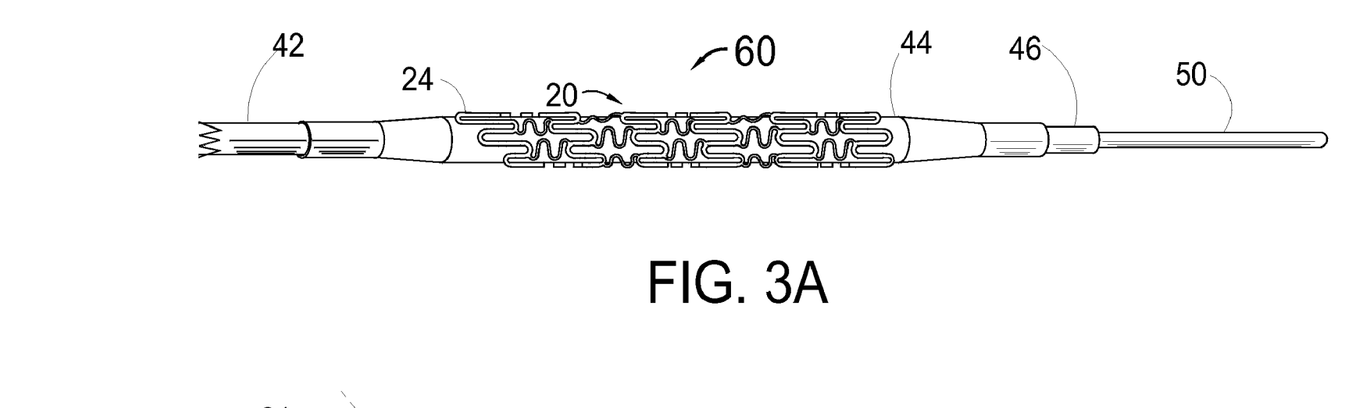
FIG. 3A illustrates a distal portion of a stent delivery catheter having the present invention (which is a side branch stent) mounted onto that catheter.

FIG. 3A is a sketch of a distal potion of the stent delivery catheter for the side branch stent 20 mounted on a stent delivery catheter 60. The stent 20 is mounted onto a balloon 44 attached to distal shaft 46 and proximal shaft 42 of the stent delivery catheter 60. A guide wire 50 is also shown in FIG. 3A. The most proximal set of strut members 24 is seen with its angulated shape such that the stent delivery catheter 60 must be rotated during stent delivery to align the set of strut members 24 with the ostium of a side branch.

FIG. 3A can represent any of the three types of stent delivery catheters; namely: (1) a fixed wire, (2) over-the-wire or (3) rapid exchange type stent delivery catheter system. In an over-the-wire system, the guide wire 50 would be slideable through a lumen in the shaft 46 that extends from the distal end of the shaft 46 to the proximal end of the system 60 as is well known for over-the-wire balloon angioplasty catheters. In a rapid exchange system, the guide wire 50 would be slideable through a lumen in the shaft 46 that extends from the distal end of the shaft 46 to a location between the proximal end of the balloon 44 and the proximal end of the catheter 60. In a fixed wire system, the guide wire 50 would be permanently attached to the shaft 46 as described in Fischell, et al., U.S. patent application Ser. No. 09/444,104 incorporated by reference.

Figure 3B:
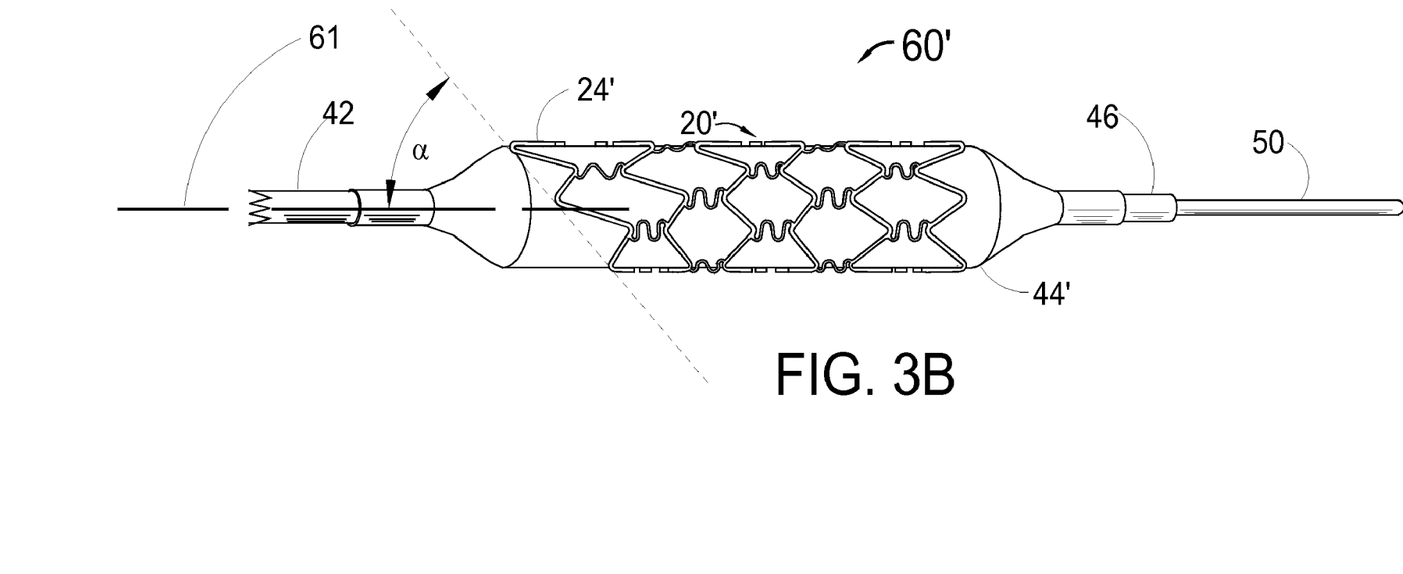
FIG. 3B illustrates the present invention stent expanded by the balloon of its stent delivery catheter.

FIG. 3B is a sketch of the present invention stent 20' as radially expanded by the inflated balloon 44' of the stent delivery catheter 60'. The expanded most proximal set of strut members 24' forms an angulation angle ≢with the longitudinal axis 61 of the stent 20'. Ideally, a side branch stent 20 should have the angulation angle ≢that is approximately equal to the angle=of the side branch as shown in FIGS. 1A and 1B. Having these two angles within ±15 degrees can provide for good support of the arterial wall at the ostium of an arterial side branch.

Figure 4A:
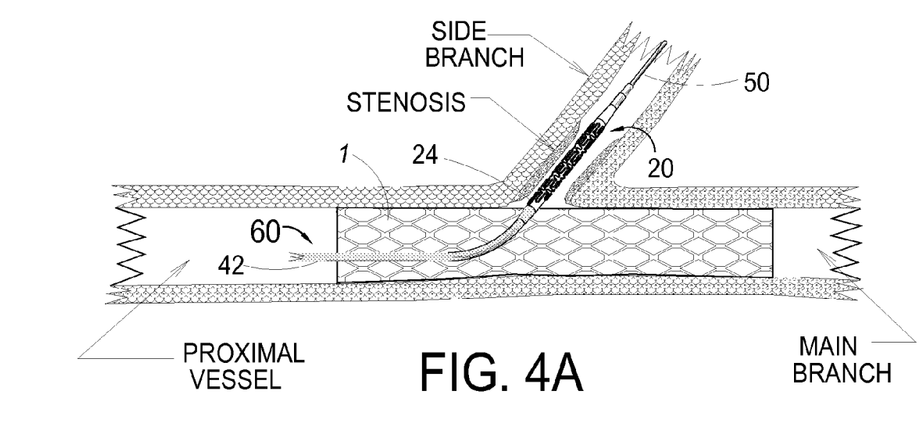
FIG. 4A is a cross section of an artery with a side branch where a first stent has placed in the main branch and the present invention stent is advanced on its stent delivery catheter before being deployed into the side ranch.

FIG. 4A is a cross section of an artery with a side branch where a first stent 1 has been placed into the proximal vessel and main branch of a bifurcated artery and the stent delivery catheter 60 of FIG. 3A has been advanced over the guide wire 50 through the struts of the stent 1 into a stenosed side branch. Once the stent 20 has been pushed through the struts of the stent 1, the proximal end (not shown) of the shaft 42 of the stent delivery catheter 60 (which proximal end is situated outside the body) is rotated by the physician until the most proximal set of strut members 24 of the stent 20 is aligned with the plane of the ostium of the side branch. The stent 20 is then deployed and the balloon catheter 60 is removed from the body.

Figure 4B:
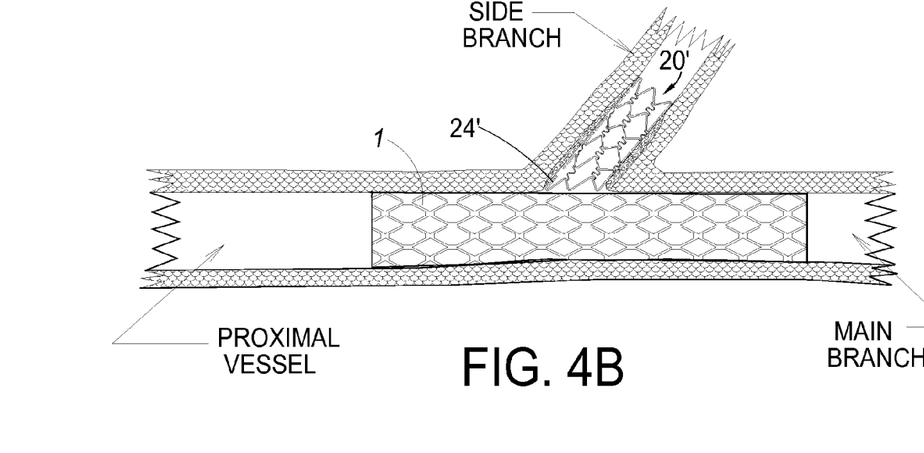
FIG. 4B is a cross section of an artery with a side branch where a first stent has been placed in the main branch and the present invention stent has been deployed in the side branch.

The result of the deployment is shown in FIG. 4B. The angulation of the most proximal set of strut members 24' of the deployed stent 20', allows the stent 20' to support the arterial wall at the ostium of the side branch without leaving an un-stented region and without having part of the stent 21' extend into the main branch. Thus the shortcomings of prior art stents as illustrated by FIGS. 1A and 1B is overcome by the improved performance of the present invention.

Figure 5A:
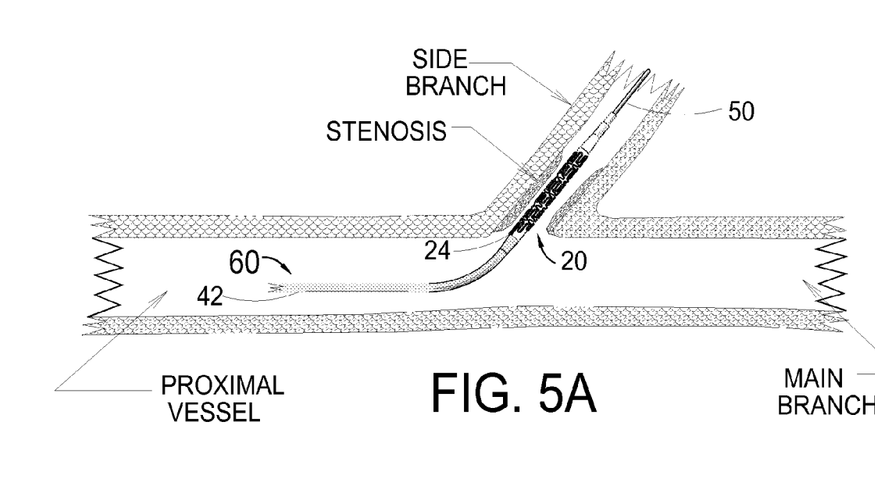
FIG. 5A is a cross section of a stent delivery catheter having a side branch stent about to be placed at the ostium of an arterial side branch.

FIG. 5A is a cross section of an artery with a side branch where the stent delivery catheter 60 and guide wire 50 have been advanced into a stenosed side branch prior to stent deployment. Once the stent 20 has been pushed into the side branch, the proximal end (not shown) of the shaft 42 of the stent delivery catheter 60 is rotated by the clinician until the plane of the most proximal set of strut members 24 of the stent 20 is approximately aligned with the plane of the ostium of the side branch. The stent 20 is then deployed and the balloon catheter 60 is removed from the body.

Figure 5B:
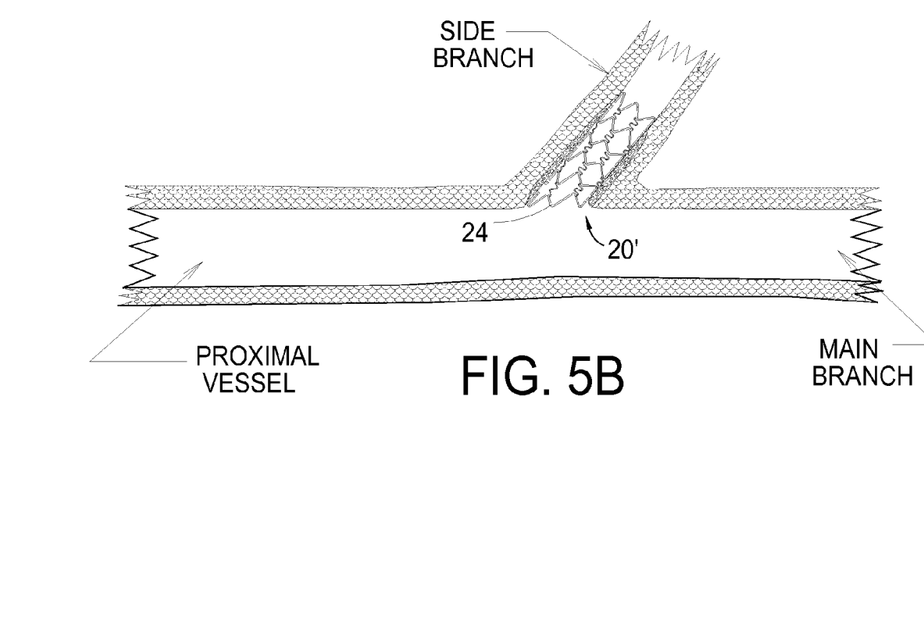
FIG. 5B is a cross section of the side branch stent of FIG. 5A as it is deployed into the side branch.

The result of the stent deployment is shown in FIG. 5B. The angulation of the most proximal set of strut members 24' of the deployed stent 20' allows the stent 20' to support the arterial wall at the ostium of the side branch without leaving an un-stented region and without extending into the main branch of the artery.

Although the descriptions herein have concentrated on application of the present invention to balloon expandable stents, it is also envisioned that a self-expanding stent having an angulated most proximal set of strut members can also be produced and deployed at the ostium of a side branch. Such a self-expanding stent could be made from Nitinol with one or more radiopaque markings.

Various other modifications adaptations, and alternative designs are of course possible in light of the above teachings. Therefore, it should be understood at this time that within the scope of the appended claims the invention may be practiced otherwise than as specifically described herein.

What is claimed is:

1. A stent comprising:
   a thin-walled, multi-cellular, tubular structure with a length and having in the unexpanded and unbent position a longitudinal axis passing through the center of the stent;
   a proximal end and a distal end;
   a multiplicity of circumferential sets of strut members, longitudinally separated each from the other and each set of strut members forming a closed, cylindrical portion of the stent;
   the stent also having a proximal set of circumferentially arranged strut members located at the proximal end of the stent and the proximal set of strut members oriented in a first plane generally transverse to the longitudinal axis;
   a distal set of circumferentially arranged strut members located at the distal end of the stent and the distal set of strut members oriented in a second plane generally transverse to the longitudinal axis; and
   a plurality of central sets of circumferentially arranged strut members positioned between the proximal and distal sets of strut members each of said central sets of circumferentially arranged stent members oriented in the same direction, and the central sets of strut members meeting the proximal set of strut members along a third plane;
   the first plane of the most proximal set of strut members having an angulation between 15 and 75 degrees with respect to the longitudinal axis of the stent when the stent has been expanded within a vessel of the human body, and the first, second and third planes intersecting with one another.

2. The stent of claim 1 wherein the stent is self-expanding.

3. The stent of claim 1 wherein the stent is balloon expandable.

4. The stent of claim 1 wherein the stent is mounted on a rapid exchange stent delivery catheter.

5. The stent of claim 1 wherein the entire stent is formed from a radiopaque metal.

6. The stent of claim 5 wherein the metal is tantalum.

7. The stent of claim 1 wherein the stent is coated with a radiopaque metal.

8. The stent of claim 7 wherein the metal is gold.

9. The stent of claim 1 wherein the proximal set of strut members is coated with a radiopaque metal.

10. The stent of claim 9 wherein the metal is gold.

11. The stent of claim 1 wherein a radiopaque marker is attached to the most proximal location on the most proximal set of strut members.

12. The stent of claim 1 wherein a radiopaque marker is attached to the most distal location on the most proximal set of strut members.

13. The stent of claim 1 wherein the sets of strut members are connected each to the other by longitudinally extending flexible links having an undulating shape.

* * * * *